United States Patent
Paris et al.

(10) Patent No.: US 11,766,656 B2
(45) Date of Patent: *Sep. 26, 2023

(54) DEVICE AND METHOD FOR PRODUCING HIGH-CONCENTRATION, LOW-TEMPERATURE NITRIC OXIDE

(71) Applicant: Origin, Inc., Princeton, NJ (US)

(72) Inventors: Michael Paris, Landsdale, PA (US); Kirill Gutsol, Warminster, PA (US); Howard Nelson, Pennington, NJ (US); David Meck, Bloomfield, NJ (US); Lindley Curameng, Fort Lee, NJ (US); Andre' DiMino, Woodcliff Lake, NJ (US)

(73) Assignee: ORIGIN, INC., Princeton, NJ (US)

( * ) Notice: Subject to any disclaimer, the term of this patent is extended or adjusted under 35 U.S.C. 154(b) by 352 days.

This patent is subject to a terminal disclaimer.

(21) Appl. No.: 17/106,311

(22) Filed: Nov. 30, 2020

(65) Prior Publication Data

US 2021/0077975 A1 Mar. 18, 2021

Related U.S. Application Data

(63) Continuation of application No. 15/841,228, filed on Dec. 13, 2017, now Pat. No. 10,850,250.
(Continued)

(51) Int. Cl.
| | | |
|---|---|---|
| *B01J 19/08* | (2006.01) | |
| *C01B 21/24* | (2006.01) | |
| *A61K 33/00* | (2006.01) | |
| *A61P 9/08* | (2006.01) | |
| *C01B 21/32* | (2006.01) | |

(Continued)

(52) U.S. Cl.
CPC ............ *B01J 19/088* (2013.01); *A61K 33/00* (2013.01); *A61P 9/08* (2018.01); *C01B 21/24* (2013.01); *C01B 21/32* (2013.01); *A61B 18/042* (2013.01); *A61M 13/003* (2013.01);
(Continued)

(58) Field of Classification Search
CPC ............ B01J 19/088; B01J 2219/0809; B01J 2219/087; B01J 2219/0871; A61P 9/08; A61K 33/00; C01B 21/24; C01B 21/32; A61B 18/042; A61M 13/003;
(Continued)

(56) References Cited

U.S. PATENT DOCUMENTS

| | | | |
|---|---|---|---|
| 2005/0218007 A1 | 10/2005 | Pekshev et al. | |
| 2006/0091116 A1* | 5/2006 | Suslov | H05H 1/42 219/121.47 |

FOREIGN PATENT DOCUMENTS

| | | |
|---|---|---|
| CN | 1730115 A | 2/2006 |
| CN | 101036482 A | 9/2007 |

(Continued)

*Primary Examiner* — Xiuyu Tai

(57) ABSTRACT

A device and method for forming NO-containing gas flow to treat a biological object is disclosed. The device may include an anode, a cathode, an interelectrode area between the cathode and the anode, an NO-containing gas flow outlet channel leading from the interelectrode area to a nozzle for directing and releasing the NO-containing gas flow from the device and a mechanism to adjust a relative position between the anode and the cathode to produce varying concentrations of NO. In addition, the device may include one or more features for interconnecting the various components to ensure proper and consistent assembly of the device.

15 Claims, 12 Drawing Sheets

Related U.S. Application Data

(60) Provisional application No. 62/434,018, filed on Dec. 14, 2016.

(51) Int. Cl.
    *A61M 13/00*     (2006.01)
    *A61B 18/04*     (2006.01)

(52) U.S. Cl.
    CPC ............... *A61M 2202/0275* (2013.01); *B01J 2219/0809* (2013.01); *B01J 2219/0871* (2013.01)

(58) Field of Classification Search
    CPC A61M 2202/0275; A61M 15/02; H05H 1/42; H05H 1/3452
    See application file for complete search history.

(56) References Cited

FOREIGN PATENT DOCUMENTS

| | | | |
|---|---|---|---|
| CN | 101828432 | A | 9/2010 |
| CN | 103648975 | A | 3/2014 |
| RU | 2553290 | C1 | 6/2015 |

\* cited by examiner

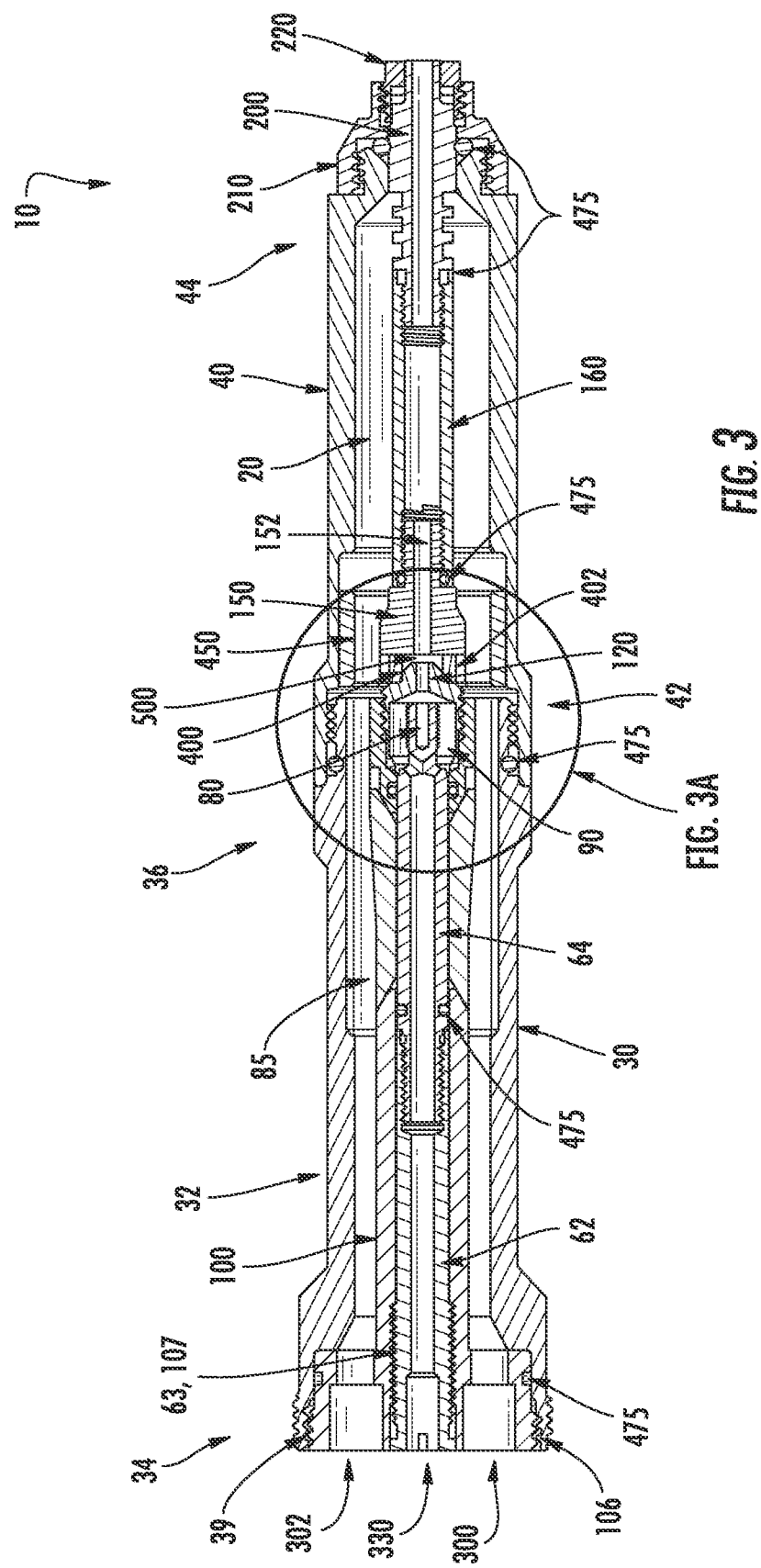

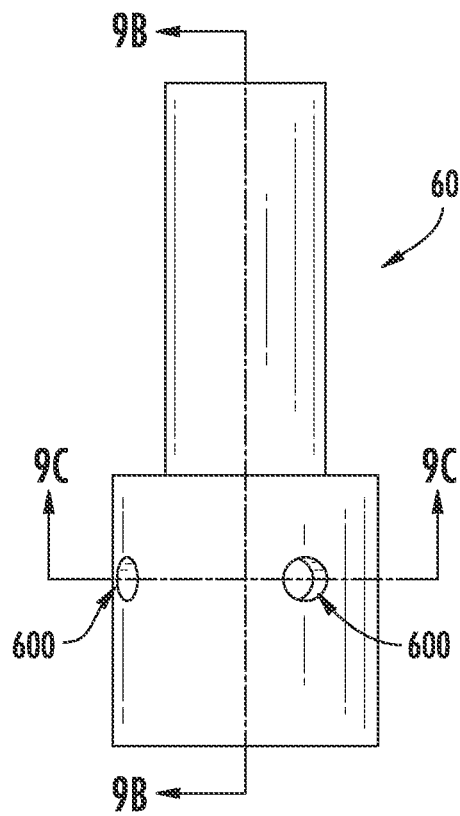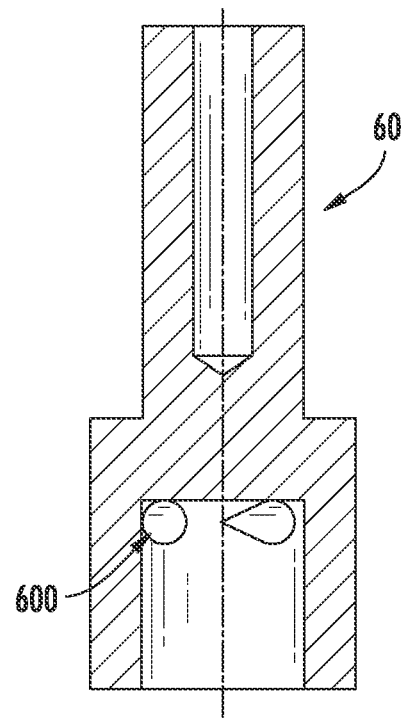
FIG. 9A  FIG. 9B
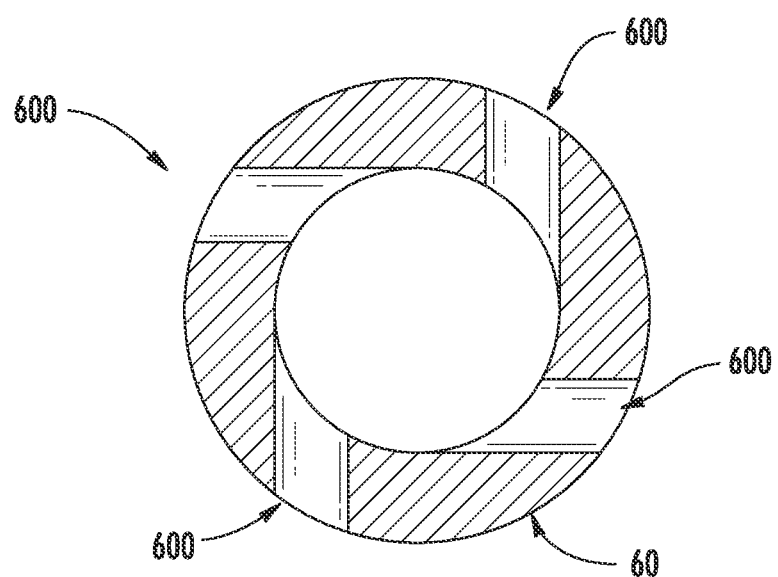
FIG. 9C

US 11,766,656 B2

DEVICE AND METHOD FOR PRODUCING HIGH-CONCENTRATION, LOW-TEMPERATURE NITRIC OXIDE

CROSS-REFERENCE TO RELATED APPLICATIONS

This is a continuation of pending U.S. Non-provisional patent application Ser. No. 15/841,228, filed Dec. 13, 2017, titled "A Device and Method for Producing High-Concentration, Low Temperature Nitric Oxide," which is a non-provisional of U.S. Provisional Patent Application Ser. No. 62/434,018, filed Dec. 14, 2016, titled "A Device and Method for Producing High-Concentration, Low Temperature Nitric Oxide," the entirety of which applications are incorporated by reference herein.

FIELD OF THE DISCLOSURE

The present disclosure generally relates to medical equipment and more specifically to devices and methods for providing treatment of a biological object with mixed gases containing nitric oxide. The disclosed methods and devices may be suitable for treating various pathological processes in general, including abdominal, thoracic, purulent, vascular and anaplastic surgery, oncology, urology, combustiology, dentistry, ophthalmology, podiatry, neurosurgery and other fields of medicine.

BACKGROUND OF THE DISCLOSURE

A device and method for preparing a mixture containing air and nitrogen for treating medical pathologies by directly supplying the mixture to a patient's tissue is known. For example, U.S. Pat. No. 7,498,000, the entire contents of which are incorporated by reference, discloses a device and method for forming a nitric oxide (NO)-containing gas flow to treat a biologic object.

NO is a pharmaceutical molecule that generates a dose related response when used to treat a biologic object. Therefore, NO must be delivered in a dosage or concentration that achieves a desired treatment effect. Due to the complexities of biological systems and tissues, NO concentrations levels required to achieve a desired effect will differ based on the application. High NO concentration levels required for one treatment may be toxic if used in a different treatment. For medical and veterinary applications, it is essential for the device to have the ability to produce NO at various concentration levels. One limitation of known devices and methods is that the concentration of NO generated is limited by the device having a fixed distance between the anode and the cathode, and matching fixed electrical parameters of the discharge.

For effective treatment, it is also important for the concentration of NO produced from the device to be consistent.

In addition, repeatable and consistent manufacturability of the device is important, but difficult to achieve. For a NO producing device to operate effectively, it is important to maintain a consistent and repeatable arc gap to control the output parameters. However, precise manufacturing of a device made from a number of interconnected components can be a challenge.

In view of the forging, it would be desirable to provide an improved device and method that overcomes the deficiencies and limitations associated with the prior art device. In addition, it would be desirable to provide an improved device that is easier to manufacture.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

Disclosed herein is an improved device for forming NO-containing plasma gas flow to treat a biological object. In one embodiment, the device may include an anode, a cathode, an interelectrode area between the cathode and the anode, an NO-containing gas flow outlet channel leading from the interelectrode area to a nozzle for directing and releasing the NO-containing gas flow from the device, and means to adjust a relative position between the anode and the cathode to produce varying concentrations of NO.

In one embodiment, the device may include a plurality of holes formed in an outer perimeter of a distal end of the cathode, the holes creating a vortex of airflow as the gas flow passes through the interelectrode area.

In one embodiment, the device may include a coolant pathway coupled to a fluid entry port and a fluid exit port so that a cooling fluid can be introduced into the device via the fluid entry port, circulated thru the device via the coolant pathway prior to exiting through the fluid exit port. The cooling fluid may be dielectric. Alternatively, the cooling fluid may be electrically conductive.

In one embodiment, the device may further include a coolant divider for separating the NO-containing gas flow outlet channel from the cooling fluid while directing the NO-containing gas to the nozzle.

In one embodiment, the device may further include an outer housing, the anode being electrically coupled to the outer housing of the device. The device may also include an insulator positioned between a portion of the cathode and a portion of the outer housing of the device to insulate the portion of the cathode from the outer housing of the device. The device may also include an interim electrode coupled to the insulator, the interim electrode positioned adjacent to a hafnium tip associated with the cathode so that an electrical arc occurs between the interim electrode and the hafnium tip, the electrical arc emanating into the interelectrode area.

In one embodiment, the outer housing of the device may include a lower shell and an upper shell. The lower shell may include a plurality of threads for engaging a corresponding plurality of threads formed on the upper shell. In one embodiment, the cathode may be located within the lower shell, the insulator being positioned between the cathode and the lower shell to insulate the cathode and the lower shell from one another.

In one embodiment, the lower shell may include a first lower coolant pathway coupled to a fluid entry port and a second lower coolant pathway coupled to a fluid exit port. The upper shell may include a first upper coolant pathway in fluid communication with the first lower coolant pathway and a second upper coolant pathway in fluid communication with the second lower coolant pathway so that, when the lower shell is coupled to the upper shell, the first and second lower coolant pathways are aligned with the first and second upper coolant pathways.

In one embodiment, the insulator may include one or more coolant entryways for providing a pathway for the cooling fluid to interact with the cathode. The one or more coolant entryways may provide a pathway for the cooling fluid to directly contact an upper portion of the cathode prior to the interelectrode area.

In one embodiment, the nozzle includes a compression nut so that rotation of the nozzle advances the anode towards the cathode, the nut including a plurality of threads for engaging a corresponding plurality of threads formed on an outer housing of the device. In one embodiment, the nozzle may further include a jacket assembly, a nozzle tip driver and a nozzle tip for releasing the NO-containing gas. The jacket assembly may be in the form of the compression nut so that rotation of the nozzle tip driver advances the anode (e.g., the nozzle tip, the coolant divider, and the arc chamber) towards the cathode. The jacket assembly may include a plurality of threads for engaging a corresponding plurality of threads formed on an outer housing of the device. The nozzle tip driver may include a plurality of threads for engaging a corresponding plurality of threads formed on the jacket assembly.

In one embodiment, the cathode may include a central hollow portion for providing a pathway for air to be forced through the cathode and into the interelectrode area.

In one embodiment, the device may further include an insulator positioned between a portion of the cathode and a portion of an outer housing of the device to insulate the cathode from the outer housing of the device. The device may also include a cathode insulator for providing a dielectric barrier between a portion of the outer housing of the device and a portion of the cathode. The insulator may be coupled to the cathode insulator by a complementary coupling feature.

In one embodiment, the complementary coupling feature may include a recess formed on one of the insulator or cathode insulator for receiving a projection formed on the other one of the insulator or cathode insulator. The cathode insulator may include an internal borehole for receiving a portion of the insulator, the recess and the projection mating with one another when the insulator is received within the internal borehole of the cathode insulator to secure a position of the cathode insulator with respect to the insulator.

In one embodiment, the device may further include an alignment bushing and a complementary coupling feature for coupling the alignment bushing to the cathode insulator. In one embodiment, the complementary coupling feature for coupling the alignment bushing to the cathode insulator may include a recess formed on one of the alignment bushing or cathode insulator for receiving a projection formed on the other one of the alignment bushing or cathode insulator to secure a position of the cathode insulator with respect to the alignment bushing.

In one embodiment, the device may also include a complementary coupling feature for coupling the alignment bushing to the coolant divider. In one embodiment, the complementary coupling feature for coupling the alignment bushing to the coolant divider may include a recess formed on one of the alignment bushing or coolant divider for receiving a projection formed on the other one of the alignment bushing or coolant divider to secure a position of the coolant divider with respect to the alignment bushing.

In one embodiment, the alignment bushing may include an internal borehole for receiving a portion of the coolant divider, the recess and the projection mating with one another when the coolant divider is received within the internal borehole of the alignment bushing to secure a position of the coolant divider with respect to the alignment bushing.

In one embodiment, the device may include an insulator positioned between a portion of the cathode and a portion of an outer housing of the device to insulate the outer housing of the device from the portion of the cathode. In addition, the device may include an interim electrode coupled to the insulator and a chamber standoff disposed between the interim electrode and the interelectrode area. The chamber standoff may be constructed of a dielectric material that prevents electrical connection.

BRIEF DESCRIPTION OF THE DRAWINGS

By way of example, specific embodiments of the disclosed device will now be described, with reference to the accompanying drawings, in which:

FIG. 3 is a second cross sectional view of the device shown in FIG. 1, taken along line 2-2 of FIG. 1;

FIG. 9A is a side view of an exemplary embodiment of a cathode tip that may be used with the device shown in FIG. 1;

FIG. 9B is a cross-sectional view of the cathode tip shown in FIG. 9A, taken along line 9B-9B in FIG. 9A;

FIG. 9C is a cross-sectional view of the cathode tip shown in FIG. 9A, taken along line 9C-9C in FIG. 9A;

DETAILED DESCRIPTION

Figure 1:
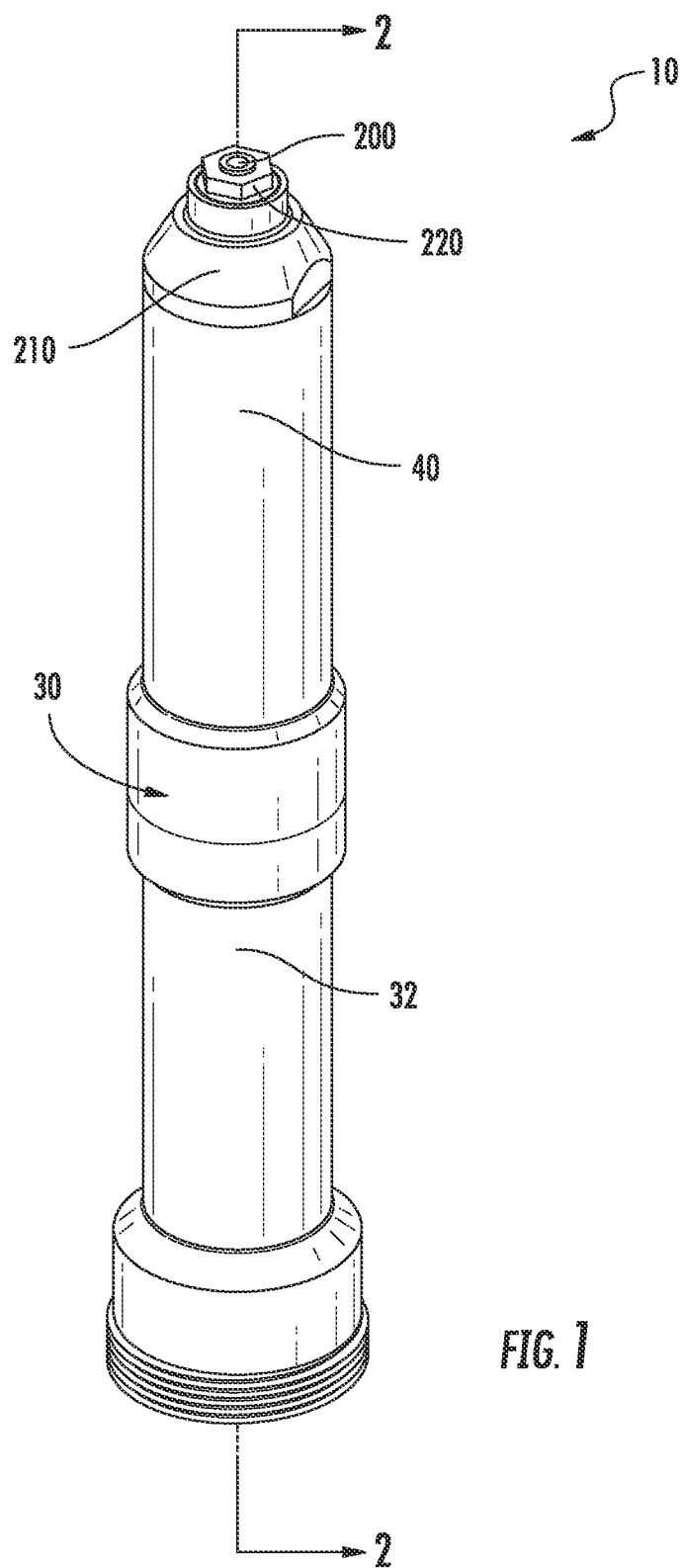
FIG. 1 is a perspective view illustrating an exemplary embodiment of an NO producing device for providing treatment of a biological object with mixed gases containing nitric oxide.

A device and method in accordance with the present disclosure will now be described more fully hereinafter with reference to the accompanying drawings, in which preferred embodiments of the device and method are shown. The disclosed device and method, however, may be embodied in many different forms and should not be construed as being limited to the embodiments set forth herein. Rather, these embodiments are provided so that this disclosure will be thorough and complete, and will fully convey the scope of the device and method to those skilled in the art. In addition, the disclosed device will be illustrated and described as containing a number of novel features, it should be understood that the device is not limited to containing all of the described features but rather the device may contain one or more of the described features. In the drawings, like numbers refer to like elements throughout.

The present disclosure describes an improved device and method for providing treatment of a biological object with mixed gases containing nitric oxide (referred to herein as NO-containing gas). Referring to FIGS. 1-4, the improved device 10 for producing and delivering NO-containing gas is shown. Generally speaking, the device 10 may form an NO-containing gas for treating a biologic object. The device 10 may form the NO-containing gas by using a DC arc discharge to generate NO in an interelectrode area 500 (e.g., an area between a cathode and an anode). As will be described in greater detail, the device 10 may be configured to produce and release, from a tip of the device 10, various concentrations of nitric oxide ("NO") in more consistent output as compared to current devices. Specifically, the device 10 may, because of one or more specifically engineered confluences of high voltage electrical arc-discharge, high velocity air impingement, and recirculating cooling fluid, produce various concentrations of NO-containing gas as compared to prior art devices so that the improved device allows for selective treatment of a specific biological object such as, for example, blood coagulation, wound healing, scar removal, disinfection, etc.

Generally speaking, the device 10 includes an anode 20, a cathode 60, an interim electrode 120 for producing NO-containing gas, and an NO-containing gas flow outlet channel 152 leading from the interelectrode area 500 to a nozzle 200 for directing and releasing the NO-containing gas flow from the device 10. In use, the anode 20 may be formed as a single component. Alternatively, the anode 20 may be manufactured from multiple components, which are then coupled together. As illustrated, the anode 20 may include a proximal anode 150, a coolant divider 160, and the nozzle 200. Moreover, as illustrated, the proximal anode 150, the coolant divider 160, and the nozzle 200 may be threadably coupled to one another, although it is envisioned that they may be coupled by any other means including, for example, welding, press-fit, etc.

By design, as will be described in greater detail below, the position of the anode 20 with respect to the cathode 60 can be adjusted to produce various concentrations of NO-containing gas. That is, referring to FIG. 3A, according to one aspect of the present disclosure, the anode 20, and more specifically, the proximal anode 150, may have a proximal surface 21. In addition, the cathode 60, and more specifically, the hafnium tip 80 may have a distal surface 61. The longitudinal distance X, as measured between the distal end 61 of the cathode 60 and the proximal surface 21 of the anode 20, can be varied to produce different NO concentrations. As will be understood, varying the offset or distance X between the distal end 61 of the cathode 60 and the proximal surface 21 of the anode 20, varies the amount of voltage needed to be applied to the cathode 60 to maintain the plasma arc, and thus varies the NO concentration in the gas. In use, the distance X between the distal end 61 of the cathode 60 and the proximal surface 21 of the anode 20 can be adjusted by any suitable mechanism now known or hereafter developed including, but not limited to, those mechanism described herein.

The device 10 may also include an outer housing 30. The outer housing 30 may comprise the exterior housing or enclosure of the device 10. In addition, in use and as will be described in greater detail below, the outer housing 30 acts or receives an electrical ground. Moreover, the outer housing 30 acts as a container or housing for containing and directing fluid within the device 10. In the illustrated embodiment, the outer housing 30 may be formed from two components, e.g., a lower shell 32 and an upper shell 40, for ease of assembly. As will be described in greater detail below, the lower shell 32 and the upper shell 40 may be threadably coupled to one another, although it is envisioned that they may be coupled by other means including being manufactured as a single component.

The cathode 60 may be formed as a single component. Alternatively, the cathode 60 may be manufactured from multiple components, which are then coupled together. As illustrated, the cathode 60 may include a proximal cathode 62 and a distal cathode 64. In use, the cathode 60 may be centrally located within the lower shell 32. As illustrated, the proximal cathode 62 and the distal cathode 64 may be threadably coupled to one another, although it is envisioned that they may be coupled by any other means including, for example, welding, press-fit, etc.

In one embodiment, the cathode 60 may also include a hafnium tip 80 associated with the distal cathode 64. The hafnium tip 80 may be coupled to the cathode 60 (e.g., distal cathode 64) by any means including, for example, a press-fit. In use, the hafnium tip 80 acts to provide or release electrons to stabilize or maintain the arc. Alternatively, it is envisioned that metals other than hafnium may also be used. Moreover, in an alternate embodiment, it is envisioned that the cathode may be "tip-less", for example, for high-voltage/low-current versions of the device. As previously mentioned, the position of the cathode 60 with respect to the anode 20 may be adjusted to produce various concentrations of NO-containing gas. That is, as will be described in greater detail, in one embodiment, the distance between the cathode 60 and the anode 20 may be adjusted to produce different concentrations of NO-containing gas.

The device 10 may also include an insulator 100 positioned between at least a portion of the cathode 60 and at least a portion of the outer housing 30, for example, the lower shell 32, to insulate at least a portion of the outer housing 30 from the cathode 60. As will be described in greater detail below, an interim electrode 120 may be positioned at a distal end of the insulator 100. As will be described in greater detail below, the insulator 100 may be coupled via, for example, a threaded coupling to the outer housing 30 (e.g., at a proximal end 34 of the lower shell 32). In addition, the insulator 100 may be coupled via, for example, a threaded coupling to the cathode 60 (e.g., at proximal end of the proximal cathode 62). By providing a threaded connection between the cathode 60 (e.g., the proximal cathode 62) and the insulator 100, adjustment of the relative position of the cathode 60 (and hence the hafnium tip 80 coupled to a distal end thereof) with respect to the interim electrode 120, which is coupled to the distal end of the insulator 100, can be adjustably varied to, for example, vary the NO concentration. As such, in use, the insulator 100 helps fix the spacing between the interim electrode 120 and the cathode 60. In use, when assembled, the interim electrode 120 may be positioned within or adjacent to the anode 20 (e.g., the proximal anode 150) and the cathode 60 to provide ignition and stability of the electrical arc between the anode 20 and the cathode 60.

In use, a high voltage supply can be connected to the cathode 60 while the outer housing 30 may be connected to ground. In addition, the outer housing 30 may be in electrical contact with the anode 20, for example, the upper shell 40 may be in electrical contact with the nozzle tip 200, thus enabling the anode 20 to be electrically grounded so that, in use, an arc is generated in the interelectrode area 500 (e.g., area between the cathode 60 and anode 20). That is, in use, the nozzle tip 200, the nozzle tip driver 220, and a jacket assembly 210 associated with the nozzle tip 200 may be in contact with the outer housing 30 and thus electrically grounded. The grounding may be electrically transferred to the coolant divider 160 and the proximal anode 150, which may also be grounded as a result, so that the arc is generated in the interelectrode area 500 between the cathode 60 and the anode 20. As previously mentioned, the insulator 100 may be positioned between the cathode 60 and a portion of the outer housing 30 (e.g., between the cathode 60 and a portion of the lower shell 32) to insulate at least a portion of the outer housing 30 from the cathode 60. In addition, the anode 20 and the cathode 60 are electrically insulated with respect to the interim electrode 120, which is located adjacent the hafnium tip 80. As such, the interim electrode 120 is said to have a "floating" potential. By this arrangement, the electrical arc occurs at the juncture between the interim electrode 120 and the hafnium tip 80, emanating into the interelectrode area 500. Upon being generated in the interelectrode area 500, the NO-containing gas is directed thru the NO-containing gas flow outlet channel 152 to the nozzle tip 200. Specifically, the NO-containing gas passes thru respective output flow channels formed in the proximal anode 150, the coolant divider 160 and the nozzle tip 200, which output flow channels are in line with the cathode 60 to provide the output flow of the NO-containing gas through the nozzle tip 200.

The device 10 may use any method now known or hereafter developed in order to create the DC arc discharge in the interelectrode area 500 (e.g., area between the cathode 60 and the anode 20). For example, the device 10 may include a voltage supply for applying a voltage to the cathode 60 to generate and maintain a DC arc discharge between them, wherein a positive potential is applied to the outer housing 30 and a negative potential is applied to the cathode 60. The proximal anode 150 may be in fluid communication with a pathway 330 (e.g., a central hollow portion) formed in the cathode 60 for injecting a source gas into the interelectrode area 500 (e.g., area between the cathode 60 and the anode 20), where the source gas contains at least oxygen and nitrogen. The interelectrode area 500 may also be in fluid communication with the NO-containing gas flow outlet channel 152 formed in the anode 20 (e.g., the proximal anode 150, the coolant divider 160 and the nozzle tip 200) for directing the NO-containing gas flow from the interelectrode area 500. The NO-containing gas flow outlet channel 152 may further direct the NO-containing gas flow to the nozzle tip 200 so that the NO-containing gas flow can be used to treat a biologic object. As will be understood, the NO-containing gas flow is formed in the interelectrode area 500 between the anode 20 (e.g., proximal anode 150), the interim electrode 120, and the cathode 60 from a source gas under the effect of a DC arc discharge generated and maintained in the interelectrode area 500 between the anode 20 (e.g., proximal anode 150) and the cathode 60.

The arc discharge between the anode 20 and the cathode 60 may be generated by providing an open-circuit DC voltage across the cathode 60 and forming one or a series of high-voltage pulses to generate a spark discharge between the anode 20 and cathode 60. A value of the open-circuit voltage may be selected and adjusted to provide the change of the spark discharge to a stationary arc discharge. In non-limiting exemplary embodiments, the open-circuit voltage can be at least 200 V, and the high-voltage pulse can be at least 4 kV although other value combinations of open and high pulse voltages may be implemented. Furthermore, the stationary DC arc discharge may be maintained by a current of at least 1.8 A, where the arc discharge is stabilized using the interim electrode 120 to provide steady generation of plasma in the interelectrode area 500 (e.g., area between the cathode 60 and the anode 20) across the electric arc formed between the cathode 60 and the anode 20.

Referring again to FIG. 1, the tip of the device 10 may include a jacket assembly 210, a nozzle tip driver 220 and the nozzle tip 200 for releasing the NO-containing gas. Alternatively, it is envisioned that the tip of the device 10 may be manufactured from more or less components. In the illustrated embodiment, as will be described in greater detail below, the jacket assembly 210 may be in the form of a compression nut. In use, rotation of the nozzle tip driver 220 may advance or move the anode 20 (e.g., the nozzle tip 200, the coolant divider 160, and the proximal anode 150) towards the interim electrode 120 and the cathode 60 until the anode 20 (e.g., proximal anode 150) contacts a chamber standoff, spacer or cylinder (used interchangeably herein without the intent to limit) 400 disposed between the interim electrode 120 and the anode 20 (e.g., proximal anode 150) to ensure a precise distance between the interim electrode 120 and the anode 20 (e.g., proximal anode 150).

Figure 2:
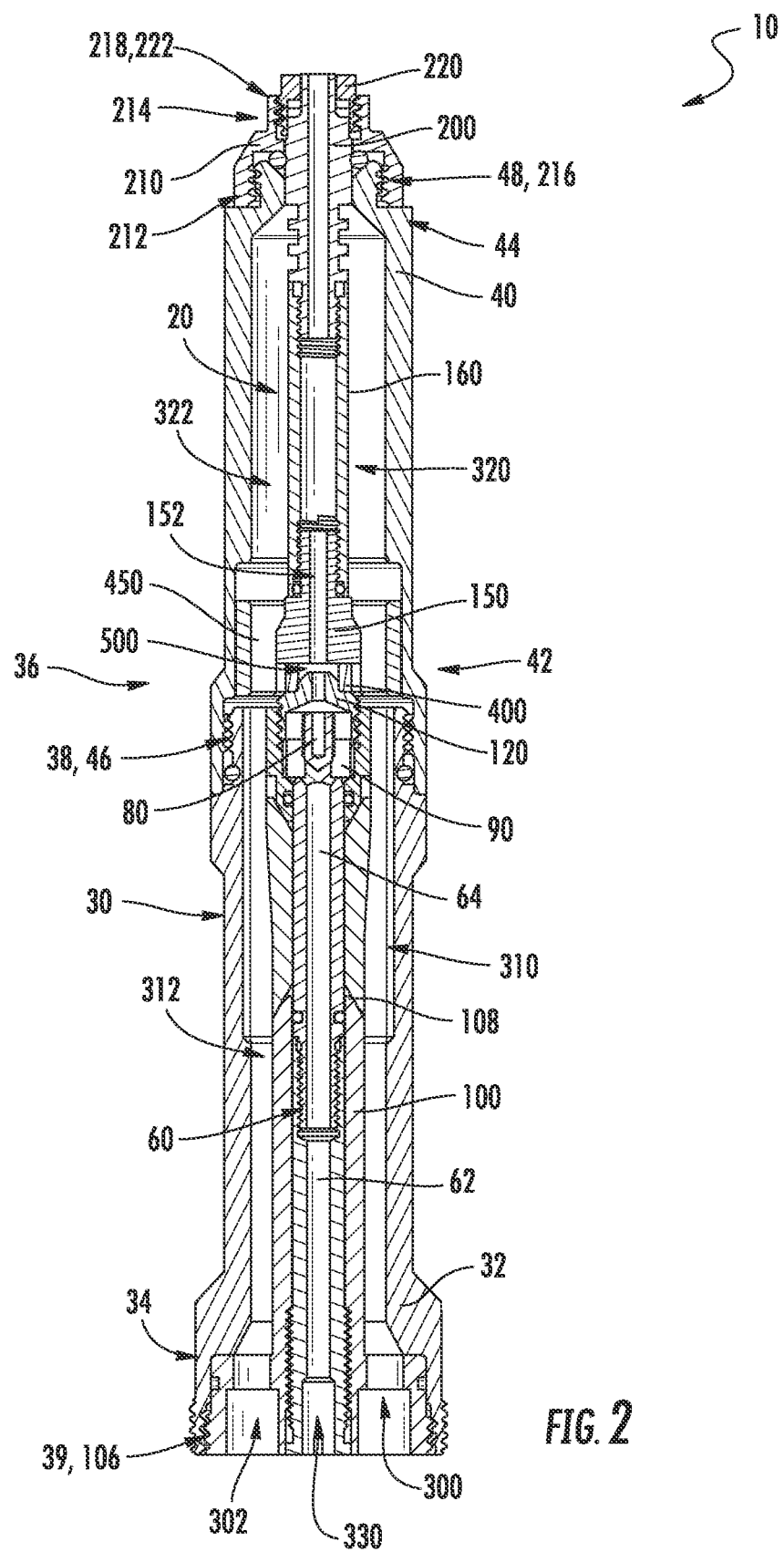
FIG. 2 is a cross sectional view of the device shown in FIG. 1, taken along line 2-2 of FIG. 1.
Figure 3A:
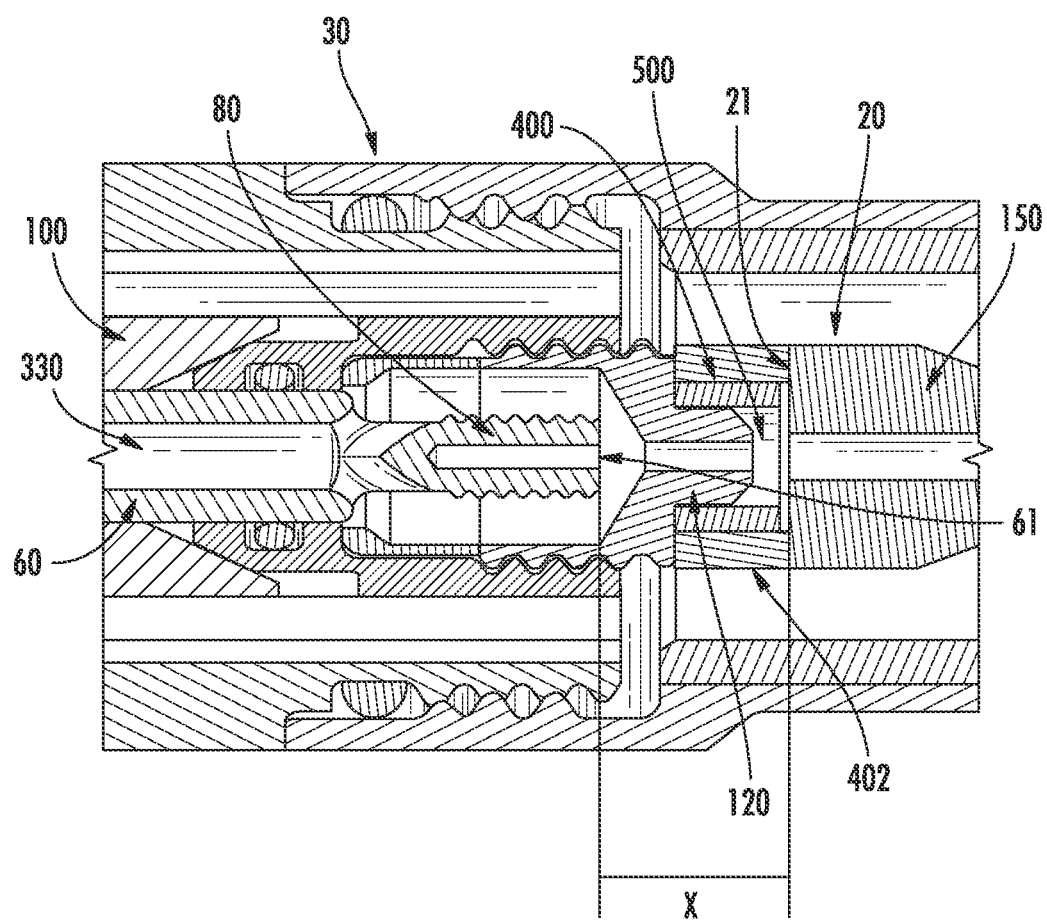
FIG. 3A is a detailed view illustrating an interelectrode area of the device shown in FIG. 3.
Figure 4:
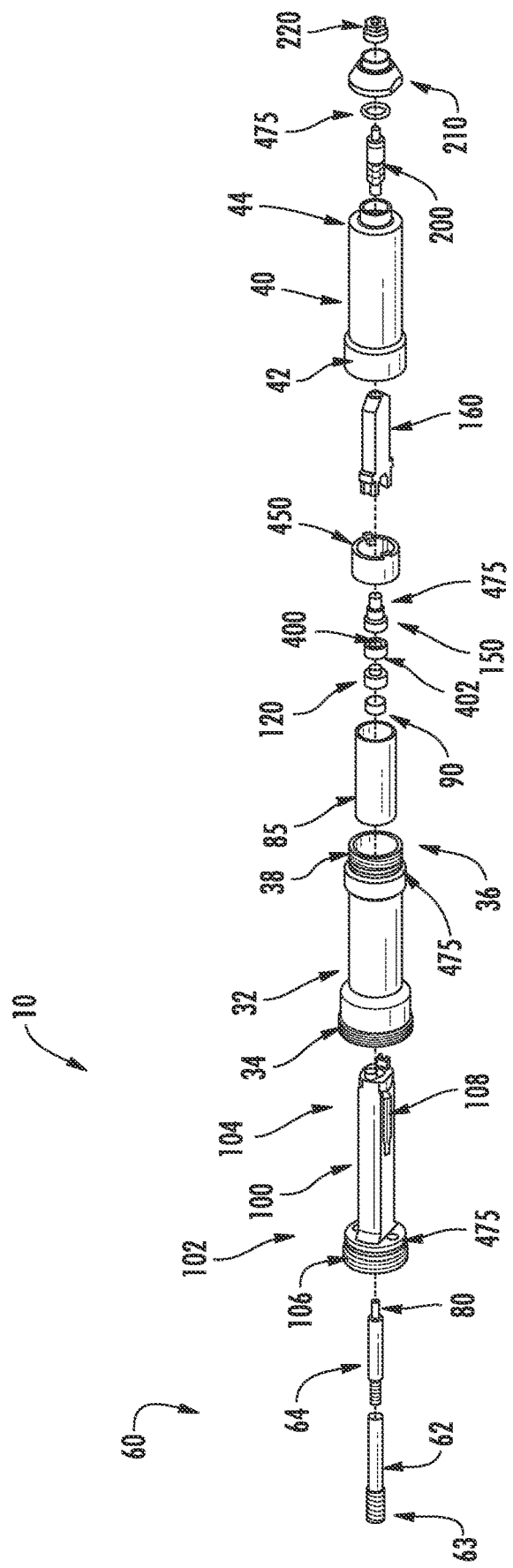
FIG. 4 is an exploded view of the device shown in FIG. 1.

As shown in FIGS. 2-4, and as previously mentioned, the outer housing 30 may be formed from two components, a lower shell 32 and an upper shell 40. The lower shell 32 may include a proximal end 34 and a distal end 36. Similarly, the upper shell 40 may include a proximal end 42 and a distal end 44. The distal end 36 of the outer housing 30 may include a plurality of threads 38 for engaging a corresponding plurality of threads 46 formed on the proximal end 42 of the upper shell 40. As previously mentioned, the proximal end 34 of the outer housing 30 may also include a plurality of internal threads 39 for engaging external threads 106 formed on a proximal end 102 of the insulator 100. In addition, the insulator 100 may include a plurality of internal threads 107 for engaging external threads 63 formed on the cathode 60 (e.g., proximal cathode 62). In use, by threadably coupling the cathode 60 to the insulator 100, a user is able to adjust the relative position of the cathode 60 (and hence the hafnium tip 80 coupled to a distal end thereof) with respect to the interim electrode 120, which is coupled to the distal end of the insulator 100, and with respect to the anode 20, to achieve a desired NO concentration. For example, in use, a user can engage a proximal end of the cathode 60 via, for example, a tool such as, but not limited to, a screw driver, a socket drive, etc. and by rotating the cathode 60 adjust the position of the cathode 60 with respect to the anode 20 and the interim electrode 120.

In addition, the jacket assembly 210 may include a proximal end 212 and a distal end 214. The distal end 44 of the upper shell 40 may include a plurality of threads 48 for engaging a corresponding plurality of threads 216 formed on the proximal end 212 of the jacket assembly 210. Similarly, the nozzle tip driver 220 may include a plurality of threads 222 for engaging a corresponding plurality of threads 218 formed on the distal end 214 of the jacket assembly 210. Tightening or loosening of the nozzle tip driver 220 when threaded in the jacket assembly 210 can allow for adjustable positioning of the anode 20 relative to the cathode 60 in order to produce various desired NO concentrations. It should be understood that while the lower shell 32, the upper shell 40, the external threads 106 formed on the insulator 100, the jacket assembly 210 and the nozzle tip driver 220 have been described and illustrated as including a plurality of threads for engaging one another, it is contemplated that the components may alternatively be coupled together by any other means now known or hereafter developed including, for example, being constructed as a single unitary component.

As previously mentioned, the lower shell 32 may enclose the cathode 60 (e.g., proximal cathode 62, distal cathode 64, and hafnium tip 80). In addition, the outer housing 30, and more specifically, the lower shell 32, may further enclose the interim electrode 120 and the insulator 100. The insulator 100 may be made from a dielectric material, such as, for example, a polymer, a ceramic, PTFE (Polytetrafluoroethylene), etc. The insulator 100 may be positioned between the cathode 60 and the outer housing 30, for example, between the cathode 60 and the lower shell 32 to insulate the cathode 60 and the lower shell 32 from one another. In addition, as previously mentioned, the insulator 100 also isolates the cathode 60 (e.g., the proximal and distal cathodes 62, 64) from the interim electrode 120. The interim electrode 120 is used to initiate the arc and maintain/stabilize the continuity of electrical discharge from the cathode 60 to the anode 20.

The device 10, and more specifically the lower shell 32, may also include a cathode insulator 85 for providing a dielectric barrier between the outer housing 30 (e.g., lower shell 32) and the cathode 60 for providing sufficient electrical insulation.

The outer housing 30, and more specifically, the upper shell 40, may enclose the anode 20 such as the proximal anode 150, the coolant divider 160 and the nozzle tip 200. In use, when the high voltage supply is connected to the cathode 60, an electrical arc is produced between the interim electrode 120 and the cathode 60 (e.g., hafnium tip 80) and onto the anode 20 thus creating the NO-containing gas plasma in the interelectrode area 500 (e.g., area between the cathode 60 and the anode 20) across the electric arc formed between the cathode 60 and the anode 20. Thereafter, the NO-containing gas is directed through the output flow channels formed in the proximal anode 150, the coolant divider 160, and the nozzle tip 200, all of which are in line with the cathode 60. In this way, an output flow of the NO-containing gas is discharged through the nozzle tip 200.

As previously mentioned, the device 10 may include one or more pathways for receiving fluid therein. Referring to FIGS. 2 and 3, in one embodiment, the device 10, and more specifically the lower shell 32 and the insulator 100 may form first and second lower coolant pathways 310, 312 coupled, respectively, to a fluid entry port 300 and a fluid exit port 302. Similarly, the device 10, and more specifically the upper shell 40 and the coolant divider 160 may form first and second upper coolant pathways 320, 322 which are in fluid communication with the first and second lower coolant pathways 310, 312, respectively. In use, when the lower shell 32 is coupled to the upper shell 40, the first and second lower coolant pathways 310, 312 are aligned with the first and second upper coolant pathways 320, 322. In this manner, a fluid (e.g., liquid, gas) may be introduced into the device 10 via the fluid entry port 300, circulated thru the device 10 via the first lower coolant pathway 310 and the first upper coolant pathway 320 located between the lower and upper shells 32, 40 and the cathode 60 and anode 20, respectively. At the distal end of the upper shell 40, the cooling fluid may be passed to the second upper coolant pathway 322, then to the second lower coolant pathway 312, where it exits through the fluid exit port 302 located at the proximal end 34 of the insulator 100. More specifically, the cooling fluid may be introduced into the device 10 at the fluid entry port 300 located at the proximal end 34 of the lower shell 32. The cooling fluid may travel the fluid pathways formed in the lower shell 32 and into the upper shell 40 adjacent to the coolant divider 160, then back down and out of the device 10 via the fluid exit port 302 located at the proximal end 34 of the lower shell 32.

In general, as the cooling fluid travels through the coolant pathways formed within the outer housing 30, heat from the NO-containing gas is transferred through the coolant divider 160 and into the cooling fluid, reducing the temperature of the NO-containing gas as it travels to the nozzle tip 200. As will be appreciated, the cooling fluid also removes heat from the anode itself.

As will be described in greater detail below, the insulator 100 may also include one or more coolant entryways 108 for providing a pathway for the cooling fluid to interact with the cathode 60. That is, the insulator 100 may include one or more coolant entryways 108 for providing a pathway for the cooling fluid to directly contact at least a portion of the cathode 60 (e.g., distal cathode 64) prior to the interim electrode 120. The configuration of these coolant entryways 108 is designed to maximize thermal draw from the cathode 60 to the cooling fluid thereby reducing the operating temperature of the cathode 60 while under load.

In one embodiment, the fluid could be electrically conductive. In contrast, dielectric fluid, such as ethylene glycol, propylene glycol, or silicone oil may be used to maximize thermal draw and to prevent the interim electrode 120 from achieving electrical potential from the cathode 60.

As illustrated, the insulator 100, the coolant divider 160, and other components located adjacent the coolant pathways 310, 320, 322, 312 may have a substantially flat or ribbed shape or surface area to allow for increased cooling of the internal components. In this manner, the contact area is maximized between the insulator 100, the coolant divider 160, and the cooling fluid, thereby enhancing heat transfer (e.g., cooling efficiency) therebetween.

In contrast with prior devices that provide cooling beyond the nozzle tip (i.e., a majority of the cooling of the NO-containing gas occurs after the NO-containing gas has exited the nozzle tip), the disclosed device 10 enables cooling, via the cooling fluid, to begin within the device 10 such as, for example, in the proximal anode 150. That is, according to one aspect of the present disclosure, the cooling fluid may interact with and cool the NO-containing gas along a substantial length of the NO-containing gas flow outlet channel 152 between the proximal anode 150 to the nozzle tip 200. In this manner, the exiting NO-containing gas is cooled to a much greater extent before it exits the device 10 as compared to prior devices. Due to the reduced temperature of the NO-containing gas exiting the nozzle tip 200, the concentration of NO-containing gas that can be immediately directed to the treatment site, which can be higher as compared to prior devices. In non-limiting exemplary embodiments, the NO-containing gas immediately exiting the nozzle tip 200 may approach 1000 degrees Celsius and exceed 20,000 ppm of NO, which may result in the NO-containing gas at the treatment site being approximately 50 degrees Celsius or less and 700 to 1,100 ppm of NO.

As previously mentioned, the cathode 60 may further include a central hollow portion that provides a pathway 330 for air to be forced through the cathode 60 and into the interelectrode area 500 for use in generating a plasma in the interelectrode area 500. Referring to FIGS. 9A, 9B and 9C, in one embodiment, the distal end of the cathode 60 may include one or more tangential holes 600. In use, the holes 600 transfer the air around the hafnium tip 80 and into the interelectrode area 500. The tangential holes 600 may be configured to create a vortex in the airflow as the gas passes through the interelectrode area 500. That is, in connection with the example embodiment of the cathode tip illustrated in FIGS. 9A, 9B and 9C, as air comes in through the central hollow portion and out the holes 600, the air swirls around the cathode 60 (e.g., hafnium tip 80). The swirling airflow surrounds the plasma and its afterglow as it goes out through the interim electrode 120 and the anode 20, which assists in in arc stabilization, resulting in a more consistent NO production.

In use, an air pump (not shown) may supply forced air through the proximal end 34 of the device 10 (via pathway 330) into the cathode 60 and forced out the nozzle tip 200. This allows the NO-containing gas created in the interelectrode area 500 to be forced up and through the nozzle tip 200 to allow it to be impinged on the treatment area.

Figure 5A:
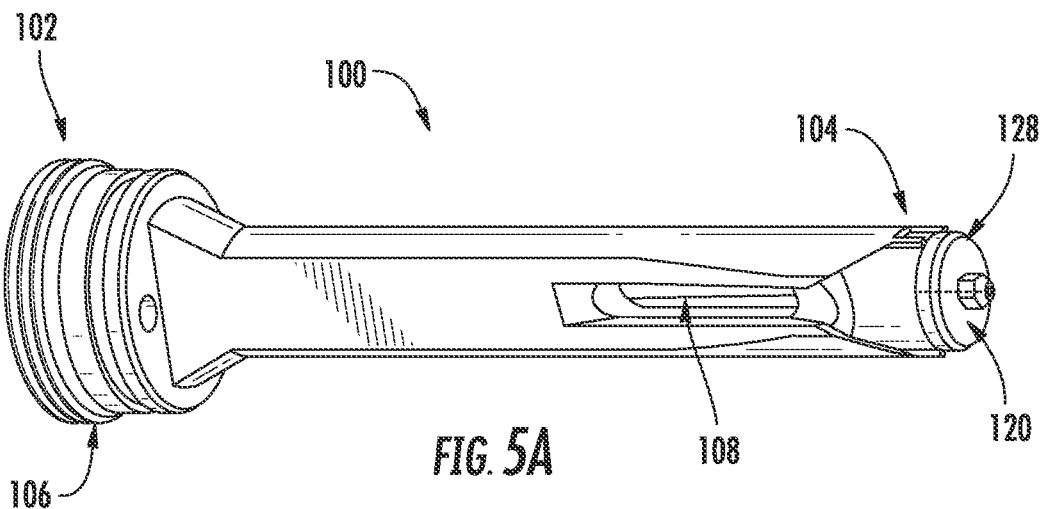
FIG. 5A is a side view an exemplary embodiment of an insulator and an exemplary embodiment of an interim electrode coupled to the insulator for use in the device shown in FIG. 1.
Figure 5B:
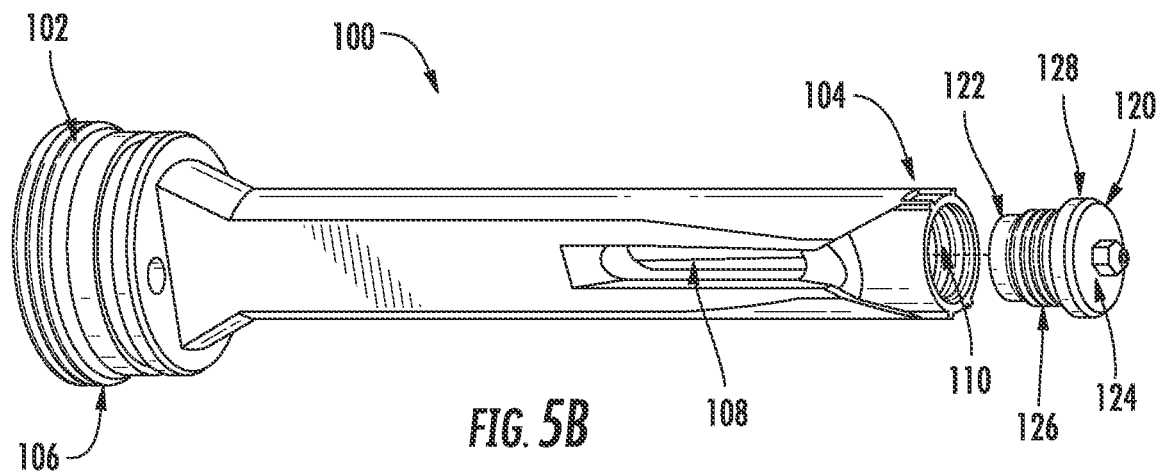
FIG. 5B is an exploded view of the insulator and interim electrode shown in FIG. 5A.

As previously mentioned, the interim electrode 120 may be coupled to the insulator 100. Referring to FIGS. 5A and 5B, the insulator 100 may include a proximal end 102, a distal end 104, a plurality of threads 106 formed on the proximal end 102 for engaging threads 39 formed on the outer housing 30, and a plurality of threads 110 (e.g., internal threads) formed on a distal end 104 thereof for threadably engaging threads 126 (e.g. external threads) formed on a proximal end 122 of the interim electrode 120. In addition, as illustrated, the interim electrode 120 may include an enlarged flange 128 formed at a distal end 124 thereof so that the interim electrode 120 may be located in a fixed position relative to the insulator 100 and the cathode 60 when the threads 126 formed on the interim electrode 120 and the threads 110 formed on the insulator 100 are fully engaged. That is, by providing a flange 128 on the interim electrode 120 to butt against the distal end 104 of the insulator 100, a consistent distance between the interim electrode 120 and the cathode 60 can be maintained. It should be noted that while the insulator 100 and the interim electrode 120 have been illustrated and described as being threadably connected, it is envisioned that they may be coupled together by other means. In addition or alternatively, the device 10 may also incorporate an interim electrode standoff 90 disposed between the distal end of the distal cathode 64 adjacent the interim electrode 120 and the hafnium tip 80. In one example embodiment, the interim electrode standoff 90 may be manufactured from a dielectric material. The interim electrode standoff 90 may be used in place of the flange 128 formed on the interim electrode to provide a precise gap distance between the distal cathode 64 and the interim electrode 120.

Figure 5C:
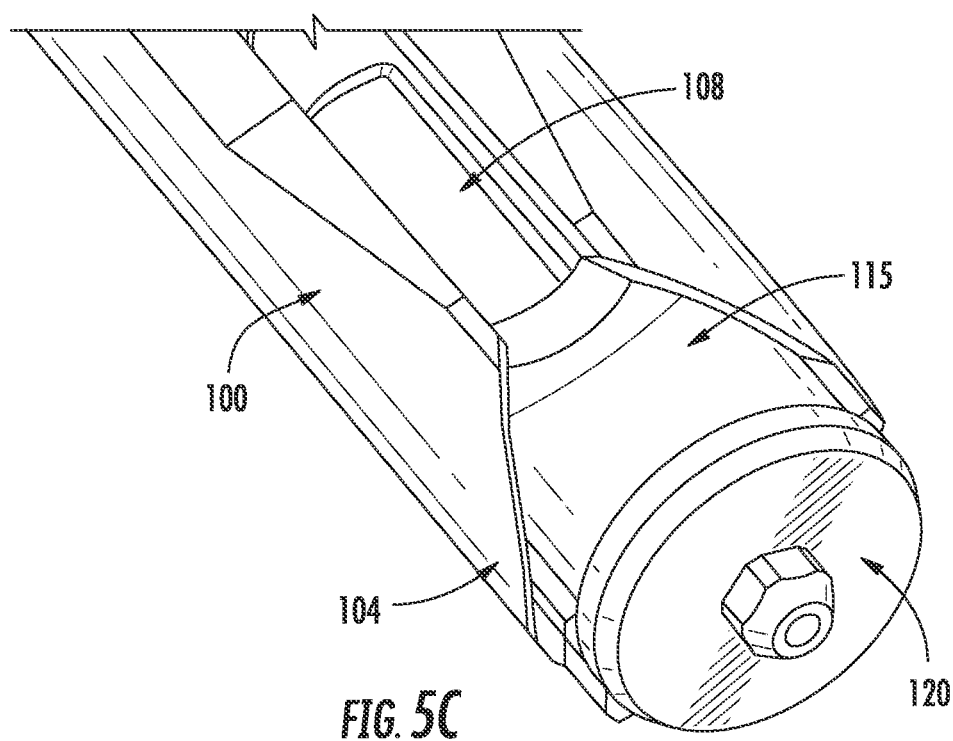
FIG. 5C is a detailed view of the insulator and interim electrode shown in FIG. 5A.

Referring to FIG. 5C, the insulator 100 may also include one or more geometric features 115 in fluid communication with the coolant entryways 108 for directly the coolant in a preferred direction to cool the interim electrode 120. That is, as illustrated, the distal end 104 of the insulator 100 may include one or more geometric features 115 such as, for example, a recessed surface, shoulders, etc. to aid in directly the exiting fluid from the coolant entryways 108 over the interim electrode 120. In this manner, an increase amount of fluid can be expected to exit the coolant entryways 108 and pass across or over the interim electrode 120.

Figure 6A:
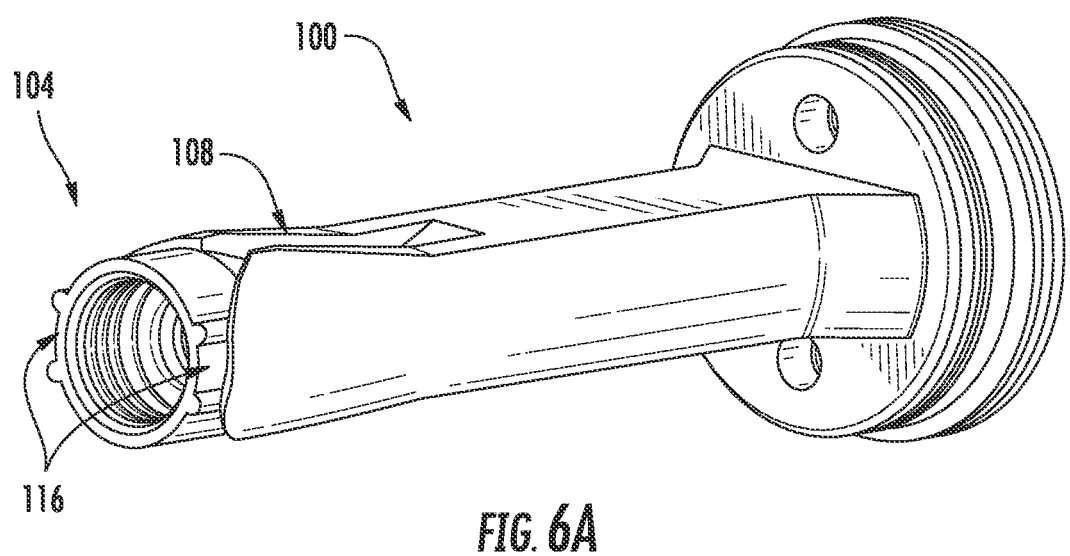
FIG. 6A is a perspective view of the insulator shown in FIG. 5A.
Figure 6B:
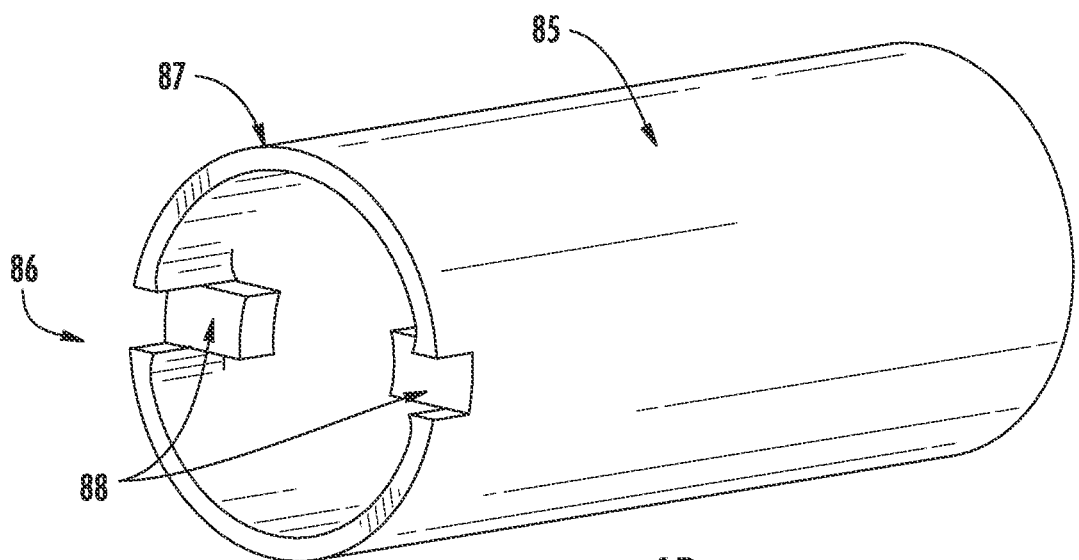
FIG. 6B is a perspective view an exemplary embodiment of a cathode insulator for use in the device shown in FIG. 1.
Figure 6C:
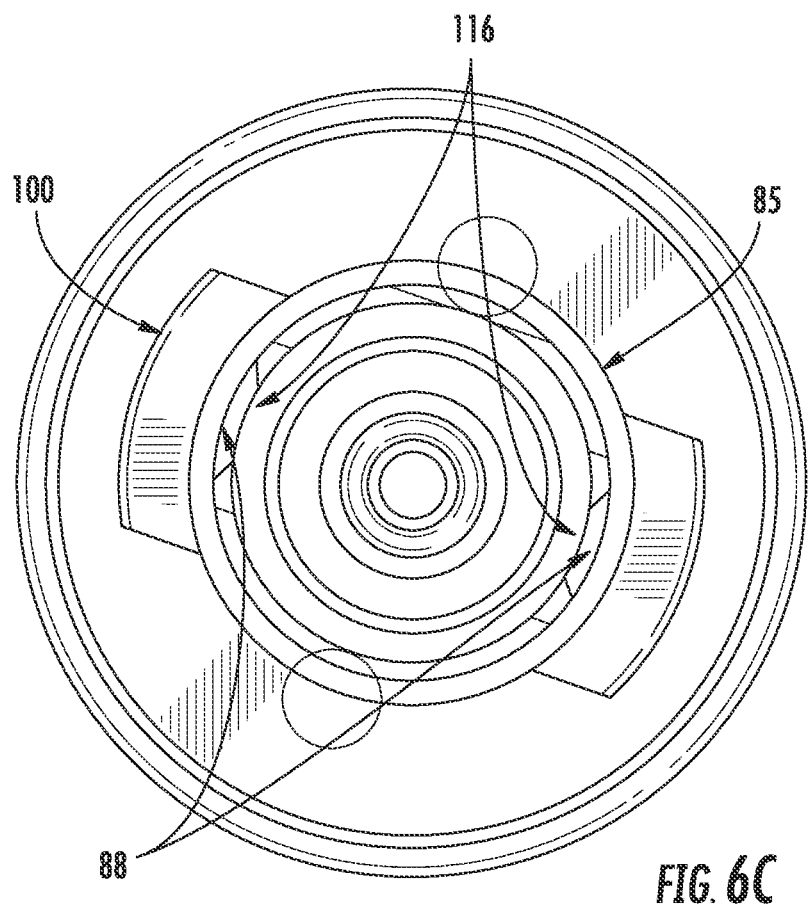
FIG. 6C is an end view of the cathode insulator shown in FIG. 6B coupled to the insulator shown in FIG. 6A.

The device 10 may further include one or more alignment features for interconnecting various components of the device 10 to facilitate assembly of the device 10. For example, referring to FIGS. 6A-6C, the insulator 100 (FIG. 6A) may include one or more complementary features for coupling to the cathode insulator 85 (FIG. 6B). By providing complementary engagement features for coupling the insulator 100 to the cathode insulator 85, the device 10 is better able to maintain a fixed, consistent alignment between the insulator 100 and the cathode insulator 85. The complementary engagement features between the insulator 100 and the cathode insulator 85 may be any suitable features now know or hereafter developed. In one example embodiment, as illustrated, the insulator 100 may include one or more recesses 116 formed in, for example, the distal end 104 of the insulator 100. Meanwhile, the cathode insulator 85 may include one or more inwardly protruding projections 88 formed on a distal end 87 thereof so that when the insulator 100 is inserted into an internal borehole 86 formed in the cathode insulator 85, the projections 88 formed on the cathode insulator 85 mate with the recesses 116 formed in the insulator 100 and thus fix the position of the insulator 100 with respect to the cathode insulator 85.

Figure 7A:
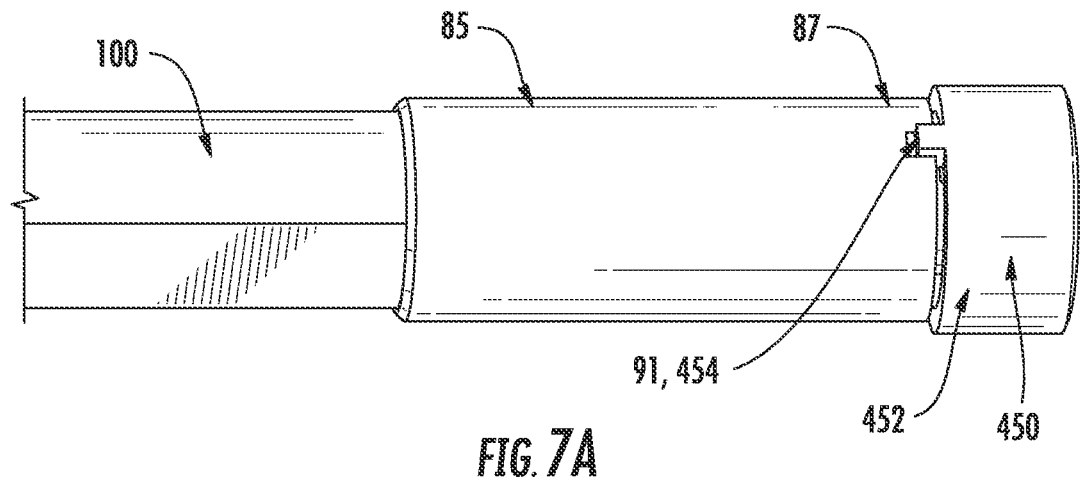
FIG. 7A is a side view an exemplary embodiment of an alignment bushing coupled to the cathode insulator shown in FIG. 6B.
Figure 7B:
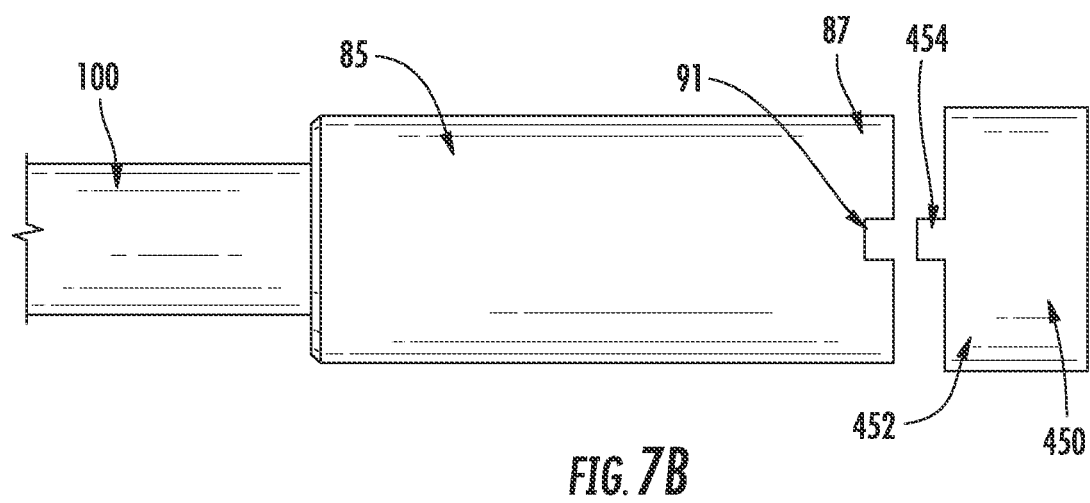
FIG. 7B is an exploded view of the alignment bushing and cathode insulator shown in FIG. 7A.

Referring to FIGS. 7A and 7B, the cathode insulator 85 may also include one or more complementary features for coupling to the alignment bushing 450, for example, to a proximal end 452 of the alignment bushing 450. By providing complementary engagement features for coupling the cathode insulator 85 to the alignment bushing 450, the device 10 is better able to maintain a fixed, consistent alignment between the cathode insulator 85 and the alignment bushing 450. The complementary engagement features between the cathode insulator 85 and the alignment bushing 450 may be any suitable features now know or hereafter developed. In one example embodiment, as illustrated, the cathode insulator 85 may include one or more recesses 91 formed in, for example, the distal end 87 of the cathode insulator 85. Meanwhile, the alignment bushing 450 may include one or more projections 454 formed on a proximal end 452 thereof so that when the cathode insulator 85 is coupled to the alignment bushing 450, the projections 454 formed on the alignment bushing 450 mate with the recesses 91 formed in the cathode insulator 85 and thus fix the position of the cathode insulator 85 with respect to the alignment bushing 450.

Figure 8A:
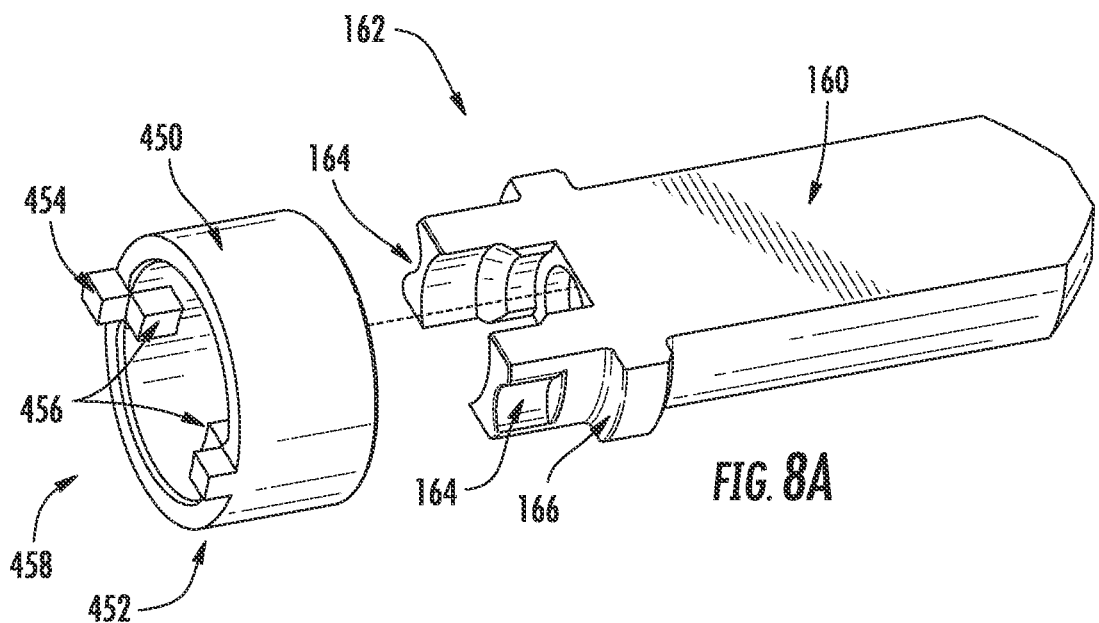
FIG. 8A is an exploded, perspective view an exemplary embodiment of a coolant divider and alignment bushing.
Figure 8B:
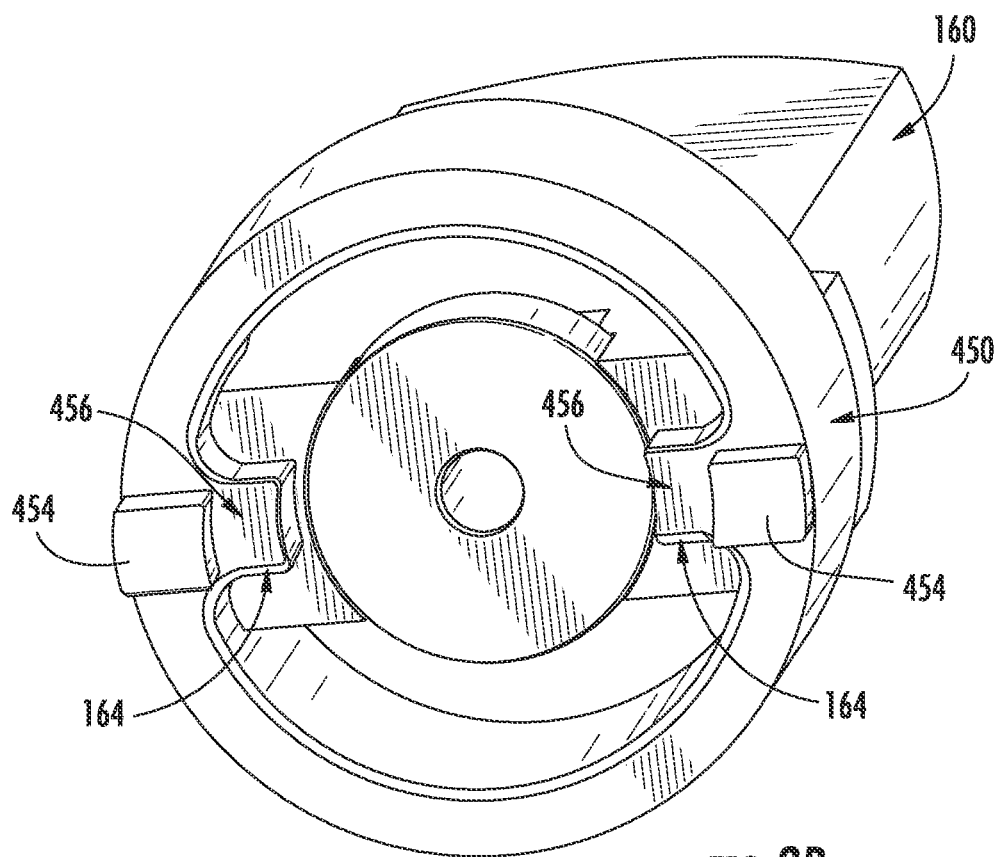
FIG. 8B is an end view of the alignment bushing coupled to the coolant divider shown in FIG. 8A.

Referring to FIGS. 8A and 8B, the alignment bushing 450 may also include one or more complementary features for coupling to the coolant divider 160. By providing complementary engagement features for coupling the alignment bushing 450 to the coolant divider 160, the device 10 is better able to maintain a fixed, consistent alignment between the alignment bushing 450 and the coolant divider 160, and thus consistent alignment of the proximal anode 150, which is coupled to the coolant divider 160, and the interim electrode 120 and the cathode 60. The complemental engagement features between the alignment bushing 450 and the coolant divider 160 may be any suitable features now know or hereafter developed. In one example embodiment, as illustrated, the coolant divider 160 may include one or more recesses 164 formed in, for example, the proximal end 162 thereof. Meanwhile, the alignment bushing 450 may include one or more inwardly protruding projections 456 formed on the proximal end 452 thereof so that when the coolant divider 160 is inserted into an internal borehole 458 formed in the alignment bushing 450, the projections 456 formed on the alignment bushing 450 mate with the recesses 164 formed in the coolant divider 160 and thus fix the position of the coolant divider 160 with respect to the alignment bushing 450. The coolant divider 160 may also include one or more stop members 166 formed thereon for providing a limit stop for inserting the coolant divider 160 into the alignment bushing 450 to provide proper spacing between the coolant divider 160 and the alignment bushing 450, and thus providing proper spacing between the proximal anode 150 and the interim electrode 120.

By manufacturing and assembling a device in accordance with the features described herein, it is contemplated that proper and consistent alignment and positioning of the various components including, for example, the distal cathode 64, the interim electrode 120, and the proximal anode 150 can be achieved when the threads 126 formed on the interim electrode 120 mate with the threads 110 formed on the insulator 100 so that the flange 128 of the interim electrode 120 contacts the distal end 104 of the insulator 100, and when after proper positioning of the various components, the jacket assembly 210 is secured onto the distal end 44 of the upper shell 40 and the nozzle tip driver 220 is threaded into engagement with the threads formed on the jacket assembly 210 so that rotation of the nozzle tip driver 220 advances the nozzle tip 200, the coolant divider 160, and the proximal anode 150 towards the cathode 60. It is also contemplated that rotation of the nozzle tip driver 220 enables adjustment of the distance between the anode 20 and the cathode 60 for varying the NO concentration.

In addition, the incorporation of complementary engagement features to couple the insulator 100 with the cathode insulator 85, to couple the alignment bushing 450 with the cathode insulator 85, and to couple the alignment bushing 450 with the coolant divider 160 helps to facilitate internal alignment of the various components of the device 10, which, in turn, assists with ensuring proper assembly of the device 10 and allows for adjustment of the spacing between the interim electrode 120, the cathode 60, and the anode 20.

Referring to FIGS. 2-4, the device 10 may further include a chamber standoff or spacer 400 disposed between the interim electrode 120 and the proximal anode 150. The chamber standoff 400 may be associated with a chamber seal 402, for example, the chamber seal 402 may be in the form of a seal for externally surrounding the chamber standoff 400, the chamber seal 402 sealing the chamber area between the interim electrode 120 and the proximal anode 150. In the illustrated embodiment, the chamber standoff 400 is adjacent to the distal end 36 of the lower shell 32 and the proximal end 42 of the upper shell 40. The chamber standoff 400 may, in some embodiments, simplify manufacturing and assembly of the device 10. That is, in combination with the nozzle tip driver 200, the chamber standoff 400 may be used to ensure a precise distance between the interim electrode 120 and the proximal anode 150 is achieved regardless of the manufacturing tolerances of the other elements of the device 10. When assembled, rotation of the nozzle tip driver 220 compresses the nozzle tip 200, the coolant divider 160, and the proximal anode 150 towards the cathode 60 until the chamber standoff 400, which is in contact with the proximal anode 150, contacts the distal surface 124 of the interim electrode 120 to provide an exact gap distance between the anode 20 and the cathode 60. As will be appreciated, providing a precisely repeatable standoff between the anode 20 and the cathode 60 can be important because it provides for a consistent arc gap thereby maintaining unit to unit output parameters. In one embodiment, the chamber standoff 400 may be manufactured from a ceramic material, although other suitable materials are envisioned.

In use, the nozzle tip driver 220 allows torqueing of the internal components (e.g., the nozzle tip 200, the coolant divider 160, the proximal anode 150, etc.) down onto the distal end of the chamber standoff 400. As mentioned, regardless of the manufacturing tolerances of these elements, by providing a highly tolerance chamber standoff 400, a high-tolerance, highly accurate standoff or spacing between the interim electrode 120 and the proximal anode 150 may be achieved. As such, the chamber standoff 400 provides a single high tolerant component, minimizing the need for the remaining components to be individually adjusted, thus greatly increasing the manufacturability, repeatability and verifiability of the device 10 simply by torqueing the nozzle tip driver 220 down onto the chamber standoff 400.

The device 10 may also include a plurality of O-rings 475 and machined grooves between components to maintain appropriate fluid seals between internal components to prevent the cooling fluid from entering the air and electrical sections (and vice versa). For example, an O-ring may be positioned between the jacket assembly 210 and the distal end 44 of the upper shell 40; between the nozzle tip 200 and the coolant divider 160; between the distal end 36 of the lower shell 32 and the proximal end 42 of the upper shell 40; between the distal cathode 64 and the insulator 100; etc.

As previously mentioned, in use, adjustment of NO concentration can be achieved by adjusting either or both of (i) the distance between the anode 20 and the cathode 60 (e.g., the relative distance between the anode 20 and the cathode 60 (hafnium tip 80), and/or (ii) the voltage applied to the cathode 60 (e.g., hafnium tip 80). As will be understood, by varying the offset or distance (e.g., distance X in FIG. 3A) between the cathode 60 and the anode 20, the amount of voltage needed to be applied to the cathode 60 to maintain the plasma arc is varied, and thus the NO concentration in the gas is also varied.

In use, the distance or relative position between the anode 20 and the cathode 60 can be achieved by any mechanism now known or hereafter developed. In one embodiment, as previously mentioned, the device may include a chamber standoff or spacer 400 disposed between the interim electrode 120 and the proximal anode 150. The chamber standoff or spacer 400 is used to provide a known, repeatable offset or distance between the anode 20 and the cathode 60. In one embodiment, the device may be provided with a plurality or set of chamber standoffs or spacers 400 having various dimensions (e.g., different widths). In use, each width would correspond to a different offset between the anode 20 and the cathode 60, and a different voltage applied to the cathode 60. The result is that each chamber standoff or spacer 400 could provide a predetermined NO concentration in the resulting gas. The various different chamber standoffs or spacers 400 providing a different concentration. As such, to adjust the NO concentration to a desired level, the user needs only to insert the corresponding chamber standoff or spacer 400 into the device and assemble the device with the anode 20 in contact with the chamber standoff or spacer 400, as previously described. Thereafter, the user tightens the nozzle tip driver 220 until the anode 20 is secured in place. The desired offset or distance between the anode 20 and the cathode 60 is automatically achieved based on the selected chamber standoff or spacer 400. For example, in one embodiment, by providing a cathode 60 to anode 20 distance of 5 mm, via for example, an appropriately sized chamber standoff or spacer 400, with 230V at 1.8 amps applied to the cathode, produces approximately 1000 ppm NO in the resulting gas stream. It will be appreciated that this example is not limiting, and that other standoff/spacer dimensions, applied voltages/currents and air flow rates can be used to adjust the concentration of NO in the resulting gas, as well as the concentration of NO in the resulting gas stream.

In an alternate embodiment, as previously mentioned, the distance between the anode 20 (e.g., proximal anode 150) and the cathode 60 (e.g., hafnium tip 80) may be adjusted by rotating the cathode 60 (e.g., proximal cathode 62) with respect to the insulator 100 using, for example, a tool such as, a screwdriver, a drive socket, etc. coupled to an appropriate recess at the proximal end of the cathode 60. In use, rotation of the cathode 60 with respect to the insulator 100 causes the mating threads to advance or retract, depending on the direction of rotation, the cathode 60 (e.g., hafnium tip 80) with respect to the anode 20 (e.g., proximal anode 150). Similar voltages would be applied (depending on the magnitude of the resulting offset) and resulting ranges of NO concentrations would be obtained. For example, one could fine tune the operation of the device by selecting an appropriately sized chamber standoff or spacer 400, then make additional, small offset adjustments using the threaded connection between the cathode 60 and the insulator 100 to slightly advance or retract the cathode 60 (e.g., hafnium tip 80).

Figure 10A:
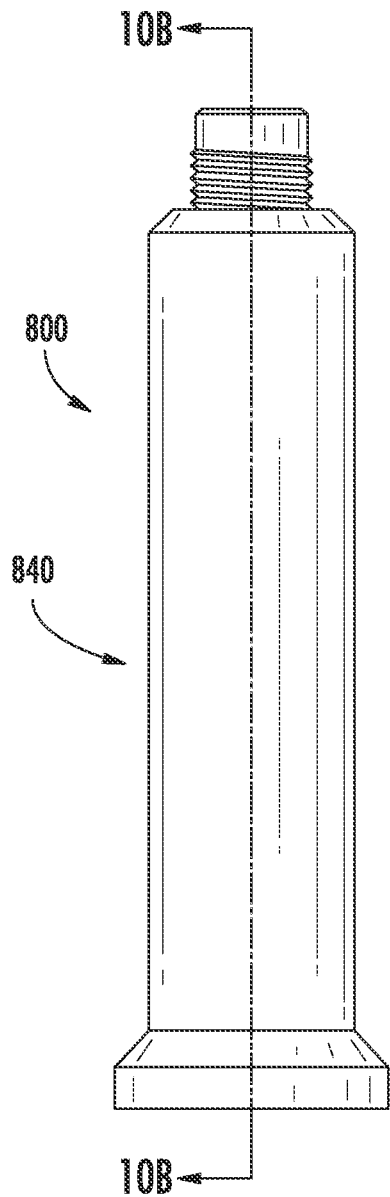
FIG. 10A is a side view of an alternate example embodiment of a threadably adjustable anode.
Figure 10B:
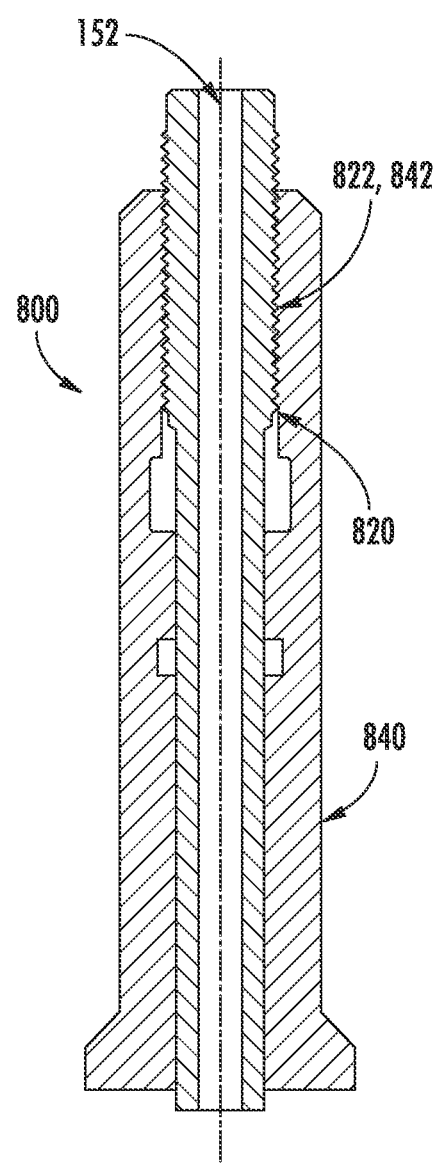
FIG. 10B is a cross-sectional view of the adjustable anode shown in FIG. 10A, taken along line 10B-10B in FIG. 10A.

In yet another embodiment, the distance between the anode 20 and the cathode 60 can be adjusted using an adjustable anode 800. Referring to FIGS. 10A and 10B, the adjustable anode 800 may include inner and outer components 820, 840, for example, an inner electrically conductive component 820 and an outer component 840. In use, the adjustable anode 800 may take the place of the anode 20 located within the outer housing 30 of the device. The inner component 820 may be functionally identical to anode 20 previously described, and may be made as a single component (as illustrated in FIGS. 10A and 10B) or from multiple components, as previously described. In use, the inner electrically conductive component 820 may be movably adjustable with respect to the outer component 840. For example, as illustrated, the inner electrically conductive component 820 may include a plurality of external threads 822 for engaging internal threads 842 formed on an inner surface of the outer component 840. As such, the distance between the anode and the cathode may be adjusted by rotating the inner component 820 of the anode with respect to the outer component 840 of the anode using, for example, a tool such as, a wrench, etc. In use, rotation of the inner component 820 of the anode with respect to the outer component 840 of the anode causes the mating threads to advance or retract, depending on the direction of rotation, the anode with respect to the cathode. Similar voltages would be applied (depending on the magnitude of the resulting offset) and resulting ranges NO concentrations would be obtained.

In yet another embodiment, the position of the cathode 60 can be moved (e.g., extended or retracted) with respect to the anode 20 by rotating the insulator 100 relative to the outer housing 30 (e.g., the lower shell 32) of the device. By adjusting the position of the insulator 100 relative to the outer housing 30, one can adjust the position of the cathode 60 relative to the anode 20.

As used herein, an element or step recited in the singular and proceeded with the word "a" or "an" should be understood as not excluding plural elements or steps, unless such exclusion is explicitly recited. Furthermore, references to "one embodiment" of the present invention are not intended to be interpreted as excluding the existence of additional embodiments that also incorporate the recited features.

While certain embodiments of the disclosure have been described herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

The invention claimed is:

1. A device for forming NO-containing plasma gas flow to treat a biological object, the device comprising:
an anode;
a cathode;
an insulator disposed about the cathode;
a cathode insulator disposed about a portion of the insulator;
a bushing coupled to an end of the cathode insulator;
an interelectrode area disposed between the cathode and the anode;
an interim electrode disposed about a proximal end of the cathode;
an interim electrode standoff coupled between the insulator and the interim electrode;
a chamber standoff coupled between the interim electrode and the anode; and
an NO-containing gas flow outlet channel leading from the interelectrode area to a nozzle for directing the NO-containing gas flow from the device;
wherein the insulator, cathode insulator, interim electrode standoff, and chamber standoff are made from a dielectric material.

2. The device in claim 1, further comprising a plurality of holes formed in an outer perimeter of a distal end of the cathode, the plurality of holes creating a vortex of fluid flow as the fluid flow passes through the interelectrode area.

3. The device of claim 2, wherein the plurality of holes comprise a plurality of tangential holes.

4. The device of claim 2, wherein the plurality of holes are configured to direct fluid from a central hollow portion of the cathode out of the plurality of holes such that the fluid swirls around the cathode to thereby surrounds the plasma and its afterglow as it goes out through the interim electrode and the anode to thereby assist in in arc stabilization.

5. The device of claim 2, wherein the interim electrode is positioned adjacent to a hafnium tip associated with the cathode to enable an electrical arc to occur between the interim electrode and the hafnium tip, the electrical arc emanating into the interelectrode area.

6. The device of claim 1, wherein the insulator includes one or more coolant entryways for providing a pathway for a cooling fluid to interact with the cathode.

7. The device of claim 1, wherein the cathode includes a central hollow portion for providing a pathway for air to be forced through the cathode and into the interelectrode area.

8. The device of claim 1, further comprising a fluid divider having first and second flat surfaces, the fluid divider arranged to separate the NO-containing gas flow outlet channel from the cooling fluid while directing the NO-containing gas to the nozzle.

9. A device for forming NO-containing plasma gas flow to treat a biological object, the device comprising:
an anode,
a cathode, and an insulator surrounding the cathode, the cathode including a plurality of tangentially arranged holes for creating a vortex of fluid flow as the fluid exits the cathode;

a cathode insulator disposed about the insulator;

a bushing coupled to the cathode insulator;

an interelectrode area between the cathode and the anode;

an interim electrode disposed about a proximal end of the cathode;

an interim electrode standoff coupled between the insulator and the interim electrode;

a chamber standoff coupled between the interim electrode and the anode; and an NO-containing gas flow outlet channel leading from the interelectrode area to a nozzle for directing the NO-containing gas flow from the device;

wherein at least one of the insulator, cathode insulator, interim electrode standoff, and chamber standoff are made from a dielectric material.

10. The device in claim 9, wherein the plurality of tangentially arranged holes are configured to creating said vortex of fluid flow as the fluid flow passes through the interelectrode area.

11. The device of claim 9, wherein the plurality of holes are configured to direct fluid from a central hollow portion of the cathode out of the plurality of holes such that the fluid swirls around the cathode to thereby surrounds the plasma and its afterglow as it goes out through the interim electrode and the anode to thereby assist in in arc stabilization.

12. The device of claim 9, wherein the interim electrode is positioned adjacent to a hafnium tip associated with the cathode to enable an electrical arc to occur between the interim electrode and the hafnium tip, the electrical arc emanating into the interelectrode area.

13. The device of claim 9, wherein the insulator includes one or more coolant entryways for providing a pathway for a cooling fluid to interact with the cathode.

14. The device of claim 9, wherein the cathode includes a central hollow portion for providing a pathway for air to be forced through the cathode and into the interelectrode area.

15. The device of claim 9, further comprising a fluid divider having first and second flat surfaces, the fluid divider arranged to separate the NO-containing gas flow outlet channel from the cooling fluid while directing the NO-containing gas to the nozzle.

\* \* \* \* \*